(12) United States Patent
Min et al.

(10) Patent No.: US 10,772,916 B2
(45) Date of Patent: Sep. 15, 2020

(54) SYSTEMS AND METHODS FOR DERIVING AND COLLECTING PLATELET PRODUCTS

(71) Applicant: Fenwal, Inc., Lake Zurich, IL (US)

(72) Inventors: Kyungyoon Min, Kildeer, IL (US); Benjamin E. Kusters, Pleasant Prairie, WI (US); Richard I. Brown, Northbrook, IL (US)

(73) Assignee: Fenwal, Inc., Lake Zurich, IL (US)

( * ) Notice: Subject to any disclaimer, the term of this patent is extended or adjusted under 35 U.S.C. 154(b) by 258 days.

(21) Appl. No.: 15/705,445

(22) Filed: Sep. 15, 2017

(65) Prior Publication Data

US 2018/0078582 A1    Mar. 22, 2018

Related U.S. Application Data

(60) Provisional application No. 62/395,536, filed on Sep. 16, 2016.

(51) Int. Cl.
| | | |
|---|---|---|
| *A61K 35/19* | (2015.01) | |
| *A61M 1/02* | (2006.01) | |
| *A61M 1/36* | (2006.01) | |
| *C12N 5/078* | (2010.01) | |

(52) U.S. Cl.
CPC ........... *A61K 35/19* (2013.01); *A61M 1/0209* (2013.01); *A61M 1/0272* (2013.01); *A61M 1/0286* (2014.02); *A61M 1/3696* (2014.02); *C12N 5/0644* (2013.01)

(58) Field of Classification Search
None
See application file for complete search history.

(56) References Cited

U.S. PATENT DOCUMENTS

| | | | |
|---|---|---|---|
| 5,632,893 | A | 5/1997 | Brown et al. |
| 5,868,696 | A | 2/1999 | Giesler et al. |
| 8,075,468 | B2 | 12/2011 | Min et al. |
| 9,079,194 | B2 | 7/2015 | Hlavinka et al. |
| 2006/0226057 | A1 | 10/2006 | Robinson et al. |
| 2008/0090714 | A1 | 4/2008 | Hudock et al. |
| 2014/0045671 | A1 | 2/2014 | Min et al. |
| 2015/0209496 | A1 | 7/2015 | Biset et al. |

FOREIGN PATENT DOCUMENTS

WO    WO 97/30715 A1    8/1997

OTHER PUBLICATIONS

Bertolini et al, Transfusion, 1992, vol. 32, No. 2, pp. 152-156. (Year: 1992).*
Abedi, Journal of Visualized Experiments, 2012, vol. 70, e 4414 (8 pages) (Year: 2012).*
European Directorate for the Quality of Medicines & HealthCare "Guide to the Preparation, Use and Quality Assurance of Blood Components" 19th Edition, 2017. p. 332-333 (Year: 2017).*
Kaufman et al , Annals of Internal Medicine, 2015, vol. 1662, No. 3, pp. 205-213 (Year: 2015).*
Rebulla et al, Transfusion Science, 1993, vol. 14, pp. 41-46. (Year: 1993).*
Terumobct, "Reveos Automated Blood Processing System for The Platelet-Rich Plasma Process", circa 2012.
Terumobct, "Trima Accel Automated Blood Collection System Version 6", circa 2013.
Terumobct, "Terumo Automated Centrifuge and Separator Integration (TACSI) for the Buffy Coat Method of Whole Blood Processing", circa 2012.
Caridianbct, "Atreus Whole Blood Processing System", circa 2008.
Extended European Search Report for Application No. 17191313.0 dated Feb. 2, 2018.

* cited by examiner

*Primary Examiner* — Allison M Fox
(74) *Attorney, Agent, or Firm* — Cook Alex Ltd.

(57) ABSTRACT

Systems and methods are provided for deriving a platelet product from a plurality of buffy coats. A plurality of buffy coats are separately collected, for example, using a conventional floor centrifuge. Plasma and/or a platelet additive solution may be added to the buffy coats. The buffy coats are pooled into a container and conveyed into a centrifuge or are sequentially conveyed into the centrifuge without being pooled, where they are continuously processed to separate platelets from the other cellular blood components. The separated platelets are conveyed out of the centrifuge as a platelet product, which may be passed through a leukocyte removal filter to reduce the white blood cell content of the platelet product. By continuously separating the buffy coats, fewer buffy coats are required to produce a single-dose platelet product, while also allowing for the derivation and collection of a plurality of single-dose platelet products.

18 Claims, 12 Drawing Sheets

SYSTEMS AND METHODS FOR DERIVING AND COLLECTING PLATELET PRODUCTS

CROSS REFERENCE TO RELATED APPLICATIONS

This application claims the benefit of and priority of U.S. Provisional Patent Application Ser. No. 62/395,536, filed Sep. 16, 2016, the contents of which are incorporated by reference herein.

BACKGROUND

Field of the Disclosure

The present subject matter relates to systems and methods for deriving and collecting platelet products. More particularly, the present subject matter relates to improved systems and methods for deriving and collecting platelet products from a plurality of buffy coats.

Description of Related Art

According to one conventional approach to generating a platelet product, whole blood from a source or donor is conveyed into a flexible container B with at least two ports R and P associated with opposing edges of the container B. The blood-filled container B is placed into a standard floor centrifuge C (FIG. 1), which is operated to separate the blood into red blood cells, platelet-poor plasma, and a buffy coat component. The container B is then removed from the centrifuge C and placed into an expresser E (FIG. 2), which applies pressure or force to the container B to express the red blood cells out of the container B via one of the ports R and to express the platelet-poor plasma out of the container B via the other port P, leaving only the buffy coat (comprised primarily of platelets, white blood cells, and residual red blood cells) in the container B.

The buffy coat produced from a single unit of whole blood is typically approximately 50 ml, with a hematocrit of approximately 50% and containing approximately $0.8 \times 10^{11}$-$1.2 \times 10^{11}$ platelets. A single-dose platelet product contains approximately $3.0 \times 10^{11}$ platelets, meaning that multiple buffy coats are required to produce a sufficient amount of platelets for a single-dose platelet product. Accordingly, the process of drawing blood, separating the blood into its constituent parts, and isolating the buffy coat is repeated several times to create a plurality of buffy coats in separate containers B. The multiple buffy coats are then pooled together in a single container V for further processing (FIG. 3). Due to separation inefficiencies and inconsistencies during further processing, five buffy coats produced from five separate whole blood donations are pooled together for creating a single platelet product.

The pooled buffy coats are mixed with plasma or platelet additive solution (typically approximately 200-250 ml) to dilute the platelets, as the platelet concentration of the pooled buffy coats is greater than the desired concentration of the platelet product. So diluting the pooled buffy coats results in a mixture with a volume of approximately 500 ml and a hematocrit of approximately 25%.

The mixture-filled container V is placed into a standard floor centrifuge C, which may be the same centrifuge C used when separating the whole blood into its constituents or may be a different floor centrifuge C. The centrifuge C is operated to separate platelets from the other cellular blood components of the pooled buffy coats, with either the platelets or the other cellular blood components being expressed from the container C (e.g., using the same expresser E as before) and the separated platelets serving as a single-dose platelet product.

On account of the separation efficiency of the floor centrifuge C, the need to dilute the pooled buffy coats, and the size of the container B, V that may be received by the centrifuge C, it is not possible to pool ten buffy coats in a single container V to produce two single-dose platelet products. In addition to this volume limitation, another potential disadvantage of this conventional method is the large amount of operator intervention required, which may increase the costs of generating a platelet product and the risk of human error. Accordingly, it would be advantageous to provide a system and method that addresses the potential shortcomings of this conventional method and system.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately as set forth in the claims appended hereto.

In one aspect, a method of deriving a platelet product from a plurality of buffy coats comprises conveying a plurality of buffy coats into a centrifuge, where platelets are continuously separated from the other cellular blood components of the plurality of buffy coats. The separated platelets are collected as a platelet product.

In another aspect, a method of deriving a platelet product from a plurality of buffy coats comprises processing blood in a first centrifuge to separate buffy coat from other blood components. The process of separating buffy coat from other blood components is repeated multiple times to generate additional buffy coats. The buffy coats are conveyed into a second centrifuge that is differently configured from the first centrifuge, where platelets are separated from the other cellular blood components of the buffy coats. The separated platelets are collected as a platelet product.

DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

According to an aspect of the present disclosure, the conventional approach to deriving a platelet product from pooled buffy coats may be improved by modifying the second separation phase, during which the pooled buffy coats are centrifuged. For example, rather than centrifuging a sealed container, pooled (or un-pooled) buffy coats may instead be passed through a flow-through separation chamber in a centrifuge, which continuously separates platelets from the other cellular blood components of the buffy coats, with the separated platelets being collected as a platelet product. By employing a flow-through separation chamber, there is no limit to the number of buffy coats that may be processed during a single procedure, whereas the conventional approach limits the buffy coat volume to the size of a container and the number of containers that may be accommodated by a floor centrifuge. Thus, a single procedure according to the present disclosure may yield multiple single-dose platelet products from larger supply of buffy coats, whereas the conventional approach may only produce one single-dose platelet product at a time from a single pool of buffy coats.

Regardless of the number of buffy coats that are processed during a single procedure according to the present disclosure, the separation efficiency of a continuous-separation centrifuge is better than that of a conventional floor centrifuge, such that a given volume of buffy coat will yield more platelet product. Where five buffy coats must be pooled to generate a single-dose platelet product in the conventional approach, fewer buffy coats must be processed according to the approach of the present disclosure in order to generate a single-dose platelet product. For example, it has been found that four or even three buffy coats (each derived from a unit of whole blood) may be sufficient to generate a single-dose platelet product using an approach according to the present disclosure, as will be described in greater detail.

Figure 5:
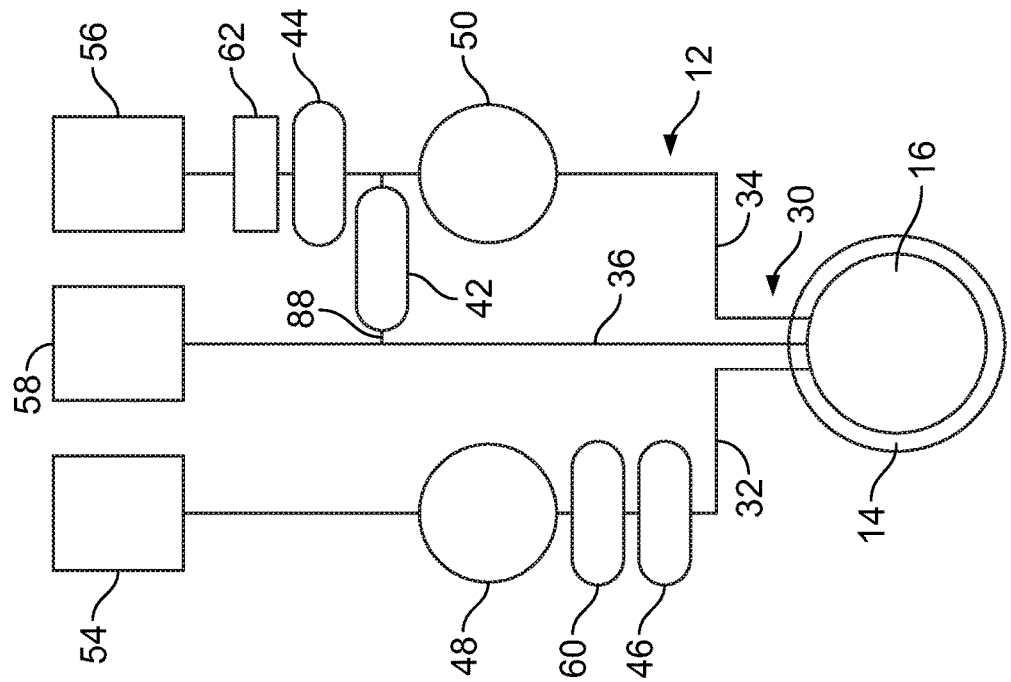
FIG. 5 is a schematic view of an exemplary fluid flow circuit that may be mounted to the fluid separation device of FIG. 4.
Figure 4:
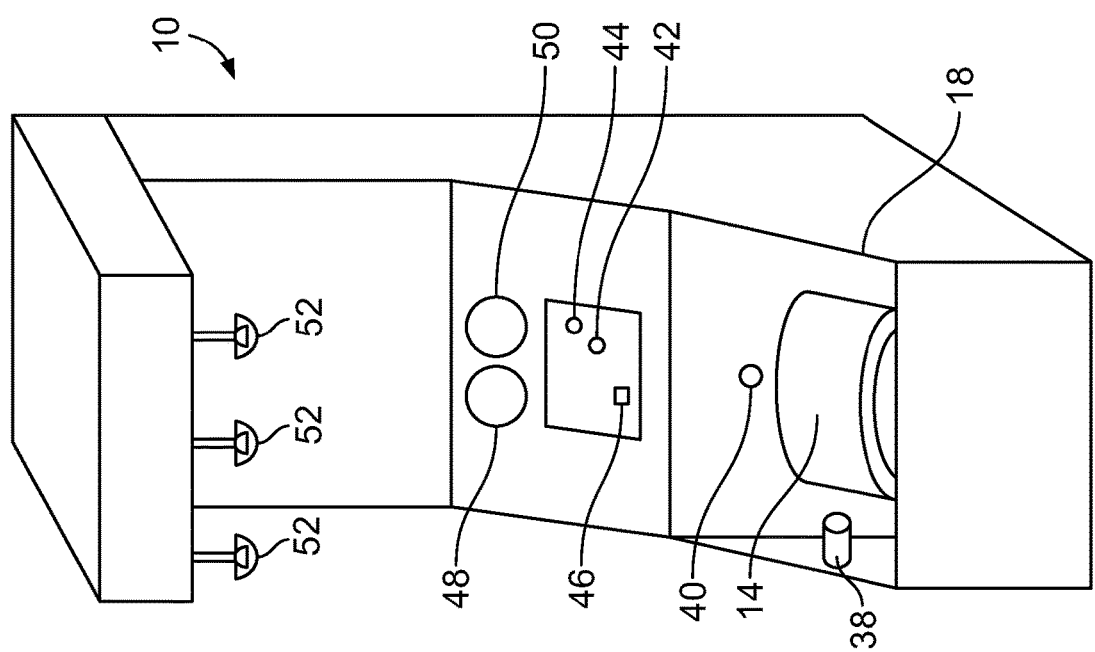
FIG. 4 is a perspective view of an exemplary fluid separation device that may be used in a buffy coat separation phase according to an aspect of the present disclosure.

The particular configuration of the continuous-separation centrifuge and associated flow-through separation chamber may vary without departing from the scope of the present disclosure. One exemplary fluid separation device 10 is shown in FIG. 4, with FIG. 5 schematically illustrating an exemplary disposable fluid flow circuit 12 that may be mounted to the durable, reusable fluid separation device 10. The fluid separation device 10 includes a centrifuge 14 (FIG. 6), which accommodates a separation chamber 16 of the fluid flow circuit 12. FIGS. 7-9A illustrate three exemplary embodiments of a rigid separation chamber 16A, 16B, 16C (collectively referred to as separation chamber 16) of the fluid flow circuit 12. It should be understood that the fluid separation device 10 of FIGS. 4 and 6, the fluid flow circuit 12 of FIG. 5, and the separation chambers 16 of FIGS. 7-9A are merely exemplary of possible configurations, and that fluid separation devices, fluid flow circuits, and separation chambers according to the present disclosure may be differently configured.

Figure 6:
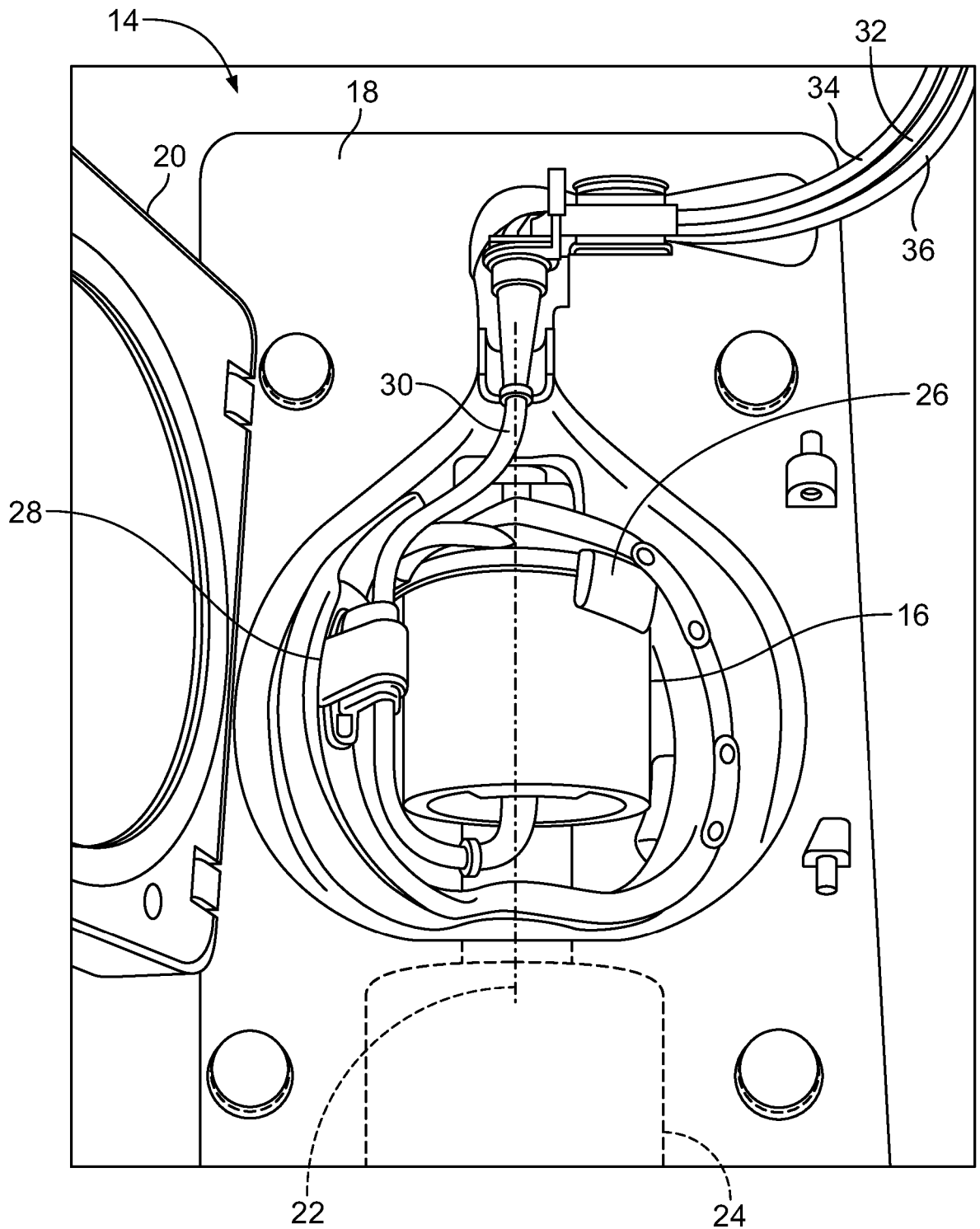
FIG. 6 is a perspective view of the centrifuge of the fluid separation device of FIG. 4, with a separation chamber of the fluid flow circuit of FIG. 5 mounted therein.

The illustrated fluid separation device 10 includes a centrifuge compartment 18 that may receive the various components of the centrifuge 14. The centrifuge compartment 18 may include a lid 20 that is opened to insert and remove a separation chamber 16 of the fluid flow circuit 12 (FIG. 6). During a separation procedure, the lid 20 may be closed with the separation chamber 16 positioned within the centrifuge compartment 18, as the separation chamber 16 is spun or rotated about an axis 22 under the power of an electric drive motor or rotor 24 of the centrifuge 14.

The particular configuration and operation of the centrifuge 14 depends upon the particular configuration of the separation chamber 16 of the fluid flow circuit 12. In one embodiment, the centrifuge 14 is similar in structure and operation to that of the ALYX® system manufactured by Fenwal, Inc. of Lake Zurich, Ill., which is an affiliate of Fresenius Kabi AG of Bad Homburg, Germany, as described in greater detail in U.S. Pat. No. 8,075,468, which is incorporated herein by reference. More particularly, the centrifuge 14 may include a carriage or support 26 that holds the separation chamber 16 and a yoke member 28. The yoke member 28 engages an umbilicus 30 of the fluid flow circuit 12, which comprises a plurality of flexible tubing conduits 32, 34, and 36 and extends from the separation chamber 16. The yoke member 28 causes the umbilicus 30 to orbit around the separation chamber 16 at a one omega rotational speed. The umbilicus 30 twists about its own axis as it orbits around the separation chamber 16. The twisting of the umbilicus 30 about its axis as it rotates at one omega with the yoke member 28 imparts a two omega rotation to the separation chamber 16, according to known design. The relative rotation of the yoke member 28 at a one omega rotational speed and the separation chamber 16 at a two omega rotational speed keeps the umbilicus 30 untwisted, thus avoiding the need for rotating seals.

Buffy coats are introduced into the separation chamber 16 by one of the conduits 32 the umbilicus 30, with the buffy coats being separated (e.g., into a layer of less dense components, such as separated platelets, and a layer of more dense components, such as white blood cells and red blood cells) within the separation chamber 16 as a result of centrifugal forces as it rotates. Components of an interface monitoring system may be positioned within the centrifuge compartment 18 to oversee separation of the buffy coats within the separation chamber 16. As shown in FIG. 4, the interface monitoring system may include a light source 38 and a light detector 40, which is positioned and oriented to receive at least a portion of the light emitted by the light source 38.

The orientation of the various components of the interface monitoring system may vary without departing from the scope of the present disclosure and depends at least in part on the particular configuration of the separation chamber 16. In general, though, the light source 38 emits a light beam (e.g., a laser light beam) through the separated blood components within the separation chamber 16 (which may be formed of a material that substantially transmits the light or at least a particular wavelength of the light without absorbing it). A portion of the light reaches the light detector 40, which transmits a signal to a controller of the fluid separation device 10. FIG. 4 shows the light detector 40 as being oriented 90° away from may the light source 38, such that light from the light source 38 travels toward the rotational axis 22 to pass through the blood components within the separation chamber 16 and is then directed along a direction generally parallel to the axis 22 to reach the light detector 40. In other embodiments, the light detector 40 may be variously positioned without departing from the scope of the present disclosure. For example, in an alternative embodiment, the light detector 40 may be positioned in the vicinity of the light source 38, such that light from the light source 38 travels toward the rotational axis 22 to pass through the blood components within the separation chamber 16 and then is reflected away from the rotational axis 22 and back through the blood components to reach the light detector 40.

The signal transmitted from the light detector 40 to the controller is indicative of the location of an interface between the separated fluid components. If the controller determines that the interface is in the wrong location (which can affect the separation efficiency of the centrifuge 14 and/or the quality of the resulting platelet product), then it can issue commands to the appropriate components of the fluid separation device 10 to modify their operation so as to move the interface to the proper location.

In addition to the centrifuge 14 and controller, the fluid separation device 10 may include other components compactly arranged to aid fluid processing. For example, the fluid separation device 10 may include a plurality of clamps or valves 42 and 44 (FIG. 4), each of which moves between a plurality of positions (e.g., between open and closed positions) to selectively contact or otherwise interact with a corresponding portion, such as a conduit or valve station, of the fluid flow circuit 12 (FIG. 5). In the closed position, a valve or clamp 42, 44 engages the associated portion of the fluid flow circuit 12 to prevent fluid flow therethrough (e.g., by pinching closed a flexible tubing conduit or closing the port of a valve station, thereby preventing fluid flow therethrough). In the open position, a valve or clamp 42, 44 is disengaged from the associated portion of the fluid flow circuit 12 (or less forcefully contacts the associated portion of the fluid flow circuit 12 than when in the closed position) to allow fluid flow therethrough (e.g., by opening the lumen of a flexible tubing conduit or opening the port of a valve station, thereby allowing fluid flow therethrough).

The fluid separation device 10 may be provided with additional components, such as a pressure sensor 46, which interact with a corresponding portion of the fluid flow circuit 12 to monitor the pressure within the fluid flow circuit 12. For example, in the illustrated embodiment, the pressure sensor 46 monitors the pressure within the separation chamber 16 during use. The controller of the fluid separation device 10 may receive signals from the pressure sensor 46 that are indicative of the pressure within the separation chamber 16 and, if a signal indicates a low- or high-pressure condition, the controller may initiate an alarm or error condition to alert an operator to the condition and/or to attempt to bring the pressure to an acceptable level without operator intervention.

The fluid separation device 10 may also include a plurality of pumps 48 and 50 to cause fluid to flow through the fluid flow circuit 12. The pumps 48 and 50 may be differently or similarly configured and/or function similarly or differently from each other. In the illustrated embodiment, the pumps 48 and 50 are configured as peristaltic pumps, which may be generally configured as described in U.S. Pat. No. 5,868,696, which is incorporated herein by reference. Each pump 48, 50 engages a different flexible tubing conduit 32, 34 of the fluid flow circuit 12 (FIG. 5) and may be selectively operated under command of the controller to cause fluid to flow through a portion of the fluid flow circuit 12.

The fluid separation device 10 may further include a plurality of weight scales 52, each of which may support one of the fluid containers 54, 56, 58 of the fluid flow circuit 12. One of the containers 54 (which may be referred to as a source container) contains the buffy coats to be separated, while the other two containers 56 and 58 are configured to receive the separated platelets and the other cellular blood components, respectively. Each weight scale 52 transmits to the controller a signal that is indicative of the weight of the fluid within the associated container 54, 56, 58 to track the change of weight during the course of a procedure. This allows the controller to process the incremental weight changes to derive fluid processing volumes and flow rates and subsequently generate signals to control processing events based, at least in part, upon the derived processing volumes. For example, the controller may diagnose leaks and obstructions in the fluid flow circuit 12 and alert an operator.

The controller is configured and/or programmed to execute a platelet product derivation procedure as described herein, but may be further configured and/or programmed to execute a variety of different fluid processing applications. In carrying out any one of these fluid processing applications, the controller is configured and/or programmed to control one or more of the following tasks: conveying fluid from a source (e.g., a fluid container 54) to the separation chamber 16, operating the centrifuge 14 to separate the fluid into two or more components, and conveying the separated components to separate destinations (e.g., into fluid containers 56 and 58). This may include instructing the centrifuge 14 to operate at a particular rotational speed and instructing a pump 48, 50 to convey fluid through a portion of the fluid flow circuit 12 at a particular flow rate. Hence, while it may be described herein that a particular component of the fluid separation device 10 (e.g., the centrifuge 14) performs a particular function, it should be understood that that component is being controlled by the controller to perform that function.

Before, during, and after a procedure, the controller may receive signals from various components of the fluid separation device 10 (e.g., the pressure sensor 46) to monitor various aspects of the operation of the fluid separation device 10 and characteristics of the fluid and separated fluid components as they flow through the fluid flow circuit 12. If the operation of any of the components and/or one or more characteristics of the fluid or separated fluid components is outside of an acceptable range, then the controller may initiate an alarm or error condition to alert the operator and/or take action to attempt to correct the condition. The appropriate corrective action will depend upon the particular error condition and may include action that is carried out with or without the involvement of an operator.

For example, the controller may include an interface control module, which receives signals from the light detector 40 of the interface monitoring system. The signals that the controller receives from the light detector 40 are indicative of the location of an interface between the separated fluid components within the separation chamber 16. If the controller determines that the interface is in the wrong location, then it can issue commands to the appropriate components of the fluid separation device 10 to modify their operation so as to move the interface to the proper location. For example, the controller may instruct one of the pumps 48, 50 to cause the buffy coats to flow into the separation chamber 16 at a different rate and/or for a separated component to be removed from the separation chamber 16 at a different rate and/or instruct the drive motor 24 of the centrifuge 16 to rotate the separation chamber 16 at a different speed.

If provided, an operator interface station associated with the controller allows the operator to view on a screen or display (in alpha-numeric format and/or as graphical images) information regarding the operation of the fluid separation device 10. The operator interface station also allows the operator to select applications to be executed by the controller, as well as to change certain functions and performance criteria of the fluid separation device 10. For example, the operator may input a desired separation efficiency or platelet yield before separation of the buffy coats begins, with the controller determining the manner in which the various components of the fluid separation device 10 are to be operated (e.g., the rate at which one of the pumps 48, 50 must be operated to achieve a particular flow rate of buffy coats into the separation chamber 16) to achieve the target separation efficiency or platelet yield.

As for the fluid flow circuit 12 (FIG. 5), it is intended to be a sterile, single use, disposable item. Before beginning a given fluid separation procedure, the operator mounts various components of the fluid flow circuit 12 to the fluid separation device 10. The controller implements the procedure based upon preset protocols, taking into account other input from the operator. Upon completing the procedure, the operator removes the fluid flow circuit 12 from association with the fluid separation device 10. The portions of the fluid flow circuit 12 holding the collected fluid component or components (e.g., platelet collection container 56) are removed from the fluid separation device 10 and retained for storage, transfusion, or further processing. The remainder of the fluid flow circuit 12 is removed from the fluid separation device 10 and discarded.

FIG. 5 illustrates one possible fluid flow circuit 12 that may be used in combination with the fluid separation device 10, but it should be understood that a variety of differently configured fluid flow circuits may also be used, with the appropriate fluid flow circuit depending on the separation procedure to be carried out using the fluid separation device 10. Generally speaking, though, the fluid flow circuit 12 includes a separation chamber 16 connected to a plurality of fluid containers 54, 56, and 58 by flexible tubing conduits 32, 34, and 36 respectively. The fluid flow circuit 12 may include additional components connected to the flexible tubing conduits, such as an air trap 60 positioned upstream of the separation chamber 16 and a leukocyte removal filter 62 positioned upstream of the platelet collection container 56.

Figure 7:
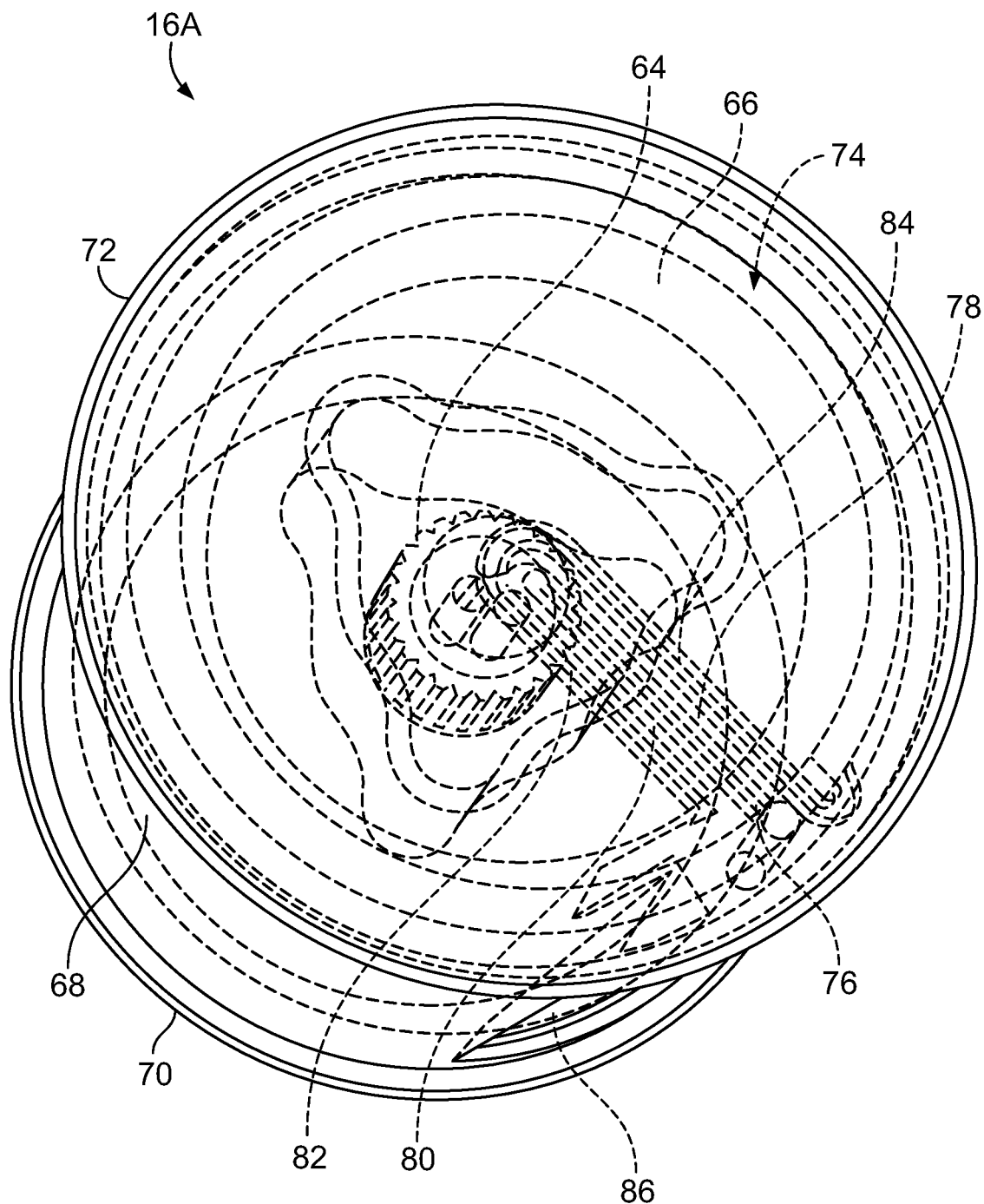
FIG. 7 is a perspective view of an exemplary separation chamber of the fluid flow circuit of FIG. 5.
Figure 7A:
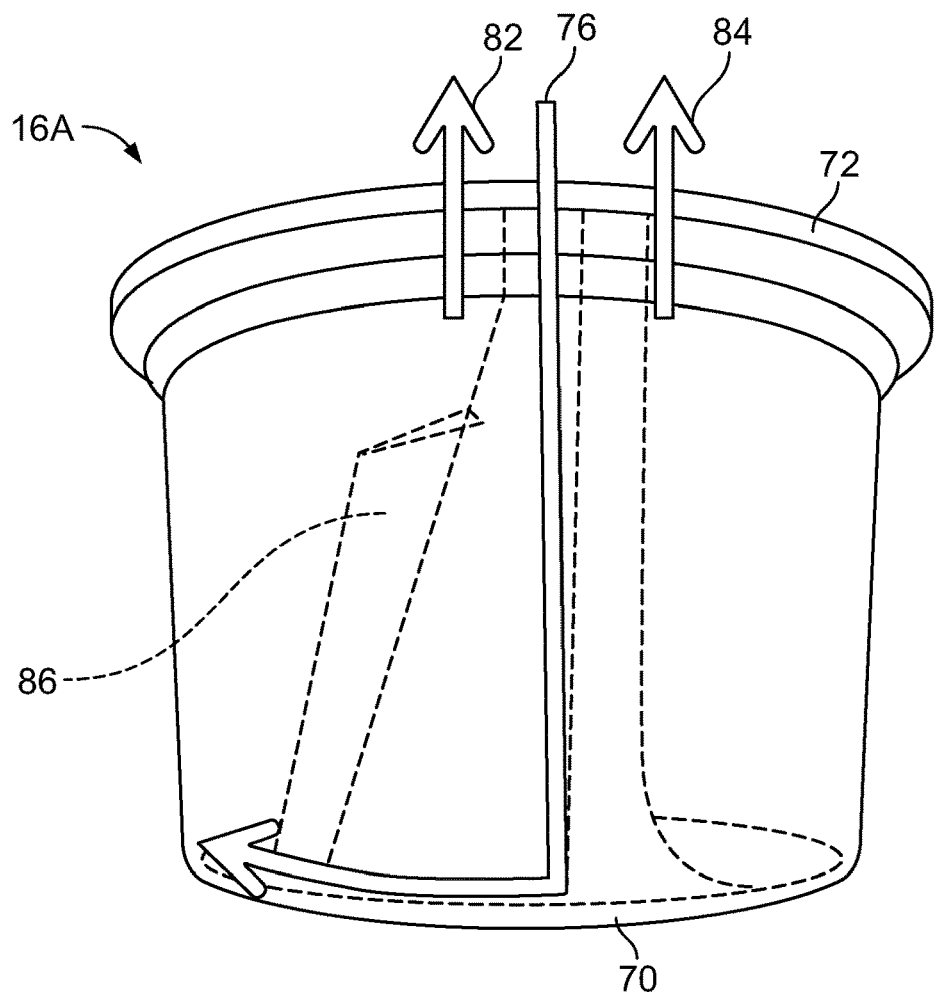
FIG. 7A is a front elevational view of the separation chamber of FIG. 7.
Figure 7B:
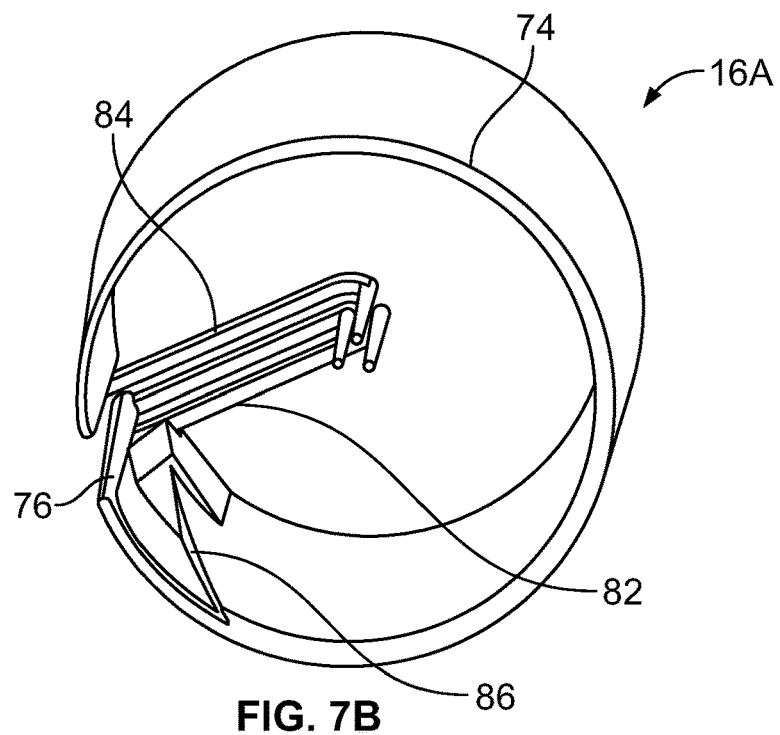
FIG. 7B is a bottom perspective view of the fluid flow path through the separation chamber of FIG. 7.

A first exemplary separation chamber 16A is shown in FIGS. 7 and 7A, while FIG. 7B illustrates the fluid flow path defined by the separation chamber 16A. In the illustrated embodiment, the body of the separation chamber 16A is pre-formed in a desired shape and configuration (e.g., by injection molding) from a rigid, biocompatible plastic material, such as a non-plasticized medical grade acrylonitrile-butadiene-styrene (ABS). The underside of the separation chamber 16A includes a shaped receptacle 64 that is suitable for receiving an end of the umbilicus 30 of the fluid flow circuit 12 (FIG. 7). A suitable receptacle 64 and the manner in which the umbilicus 30 may cooperate with the receptacle 64 to deliver fluid to and remove fluid from the separation chamber 16A are described in greater detail in U.S. Pat. No. 8,075,468.

The illustrated separation chamber 16A has radially spaced apart inner (low-g) and outer (high-g) side wall portions 66 and 68, a bottom or first end wall portion 70, and a cover or second end wall portion 72. The cover 72 comprises a simple flat part that can be easily welded or otherwise secured to the body of the separation chamber 16A. The wall portions 66 and 68, the bottom 70, and the cover 72 together define an enclosed, generally annular channel 74 (FIG. 7B).

The (buffy coat) inlet 76 communicating with the channel 74 is defined between opposing interior radial walls 78 and 80. One of the interior walls 78 joins the outer (high-g) wall portion 68 and separates the upstream and downstream ends of the channel 74. The interior walls 78 and 80 define the inlet passageway 76 of the separation chamber 16A which allows fluid to flow from the umbilicus 30 to the upstream end of the channel 74.

The illustrated separation chamber 16A further includes first and second outlets 82 and 84, respectively, which may be defined by opposing surfaces of interior radial walls. Both the first and second outlets 82 and 84 extend radially inward from the channel 74. The first (platelet) outlet 82 extends radially inward from an opening which, in the illustrated embodiment, is located at the inner side wall portion 66, while the second (other cellular components) outlet 84 extends radially inward from an opening that is associated with the outer side wall portion 68. The illustrated first outlet 82 is positioned adjacent to the inlet 76 (near the upstream end of the channel 74), while the second outlet 84 may be positioned at the opposite, downstream end of the channel 74.

Figure 8:
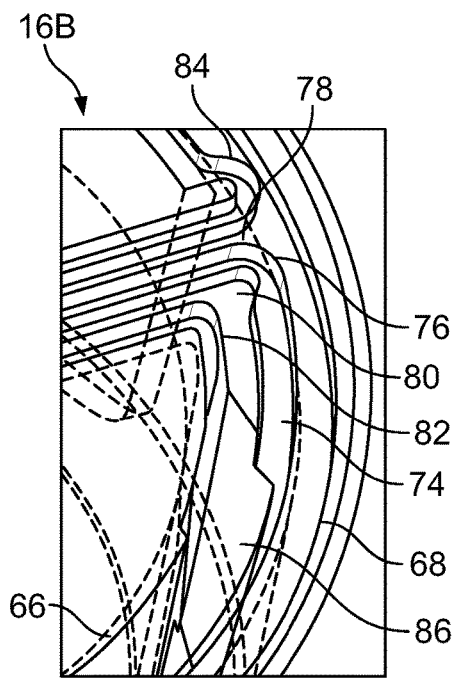
FIG. 8 is a perspective view of another embodiment of an exemplary separation chamber of the fluid flow circuit of FIG. 5.
Figure 8A:
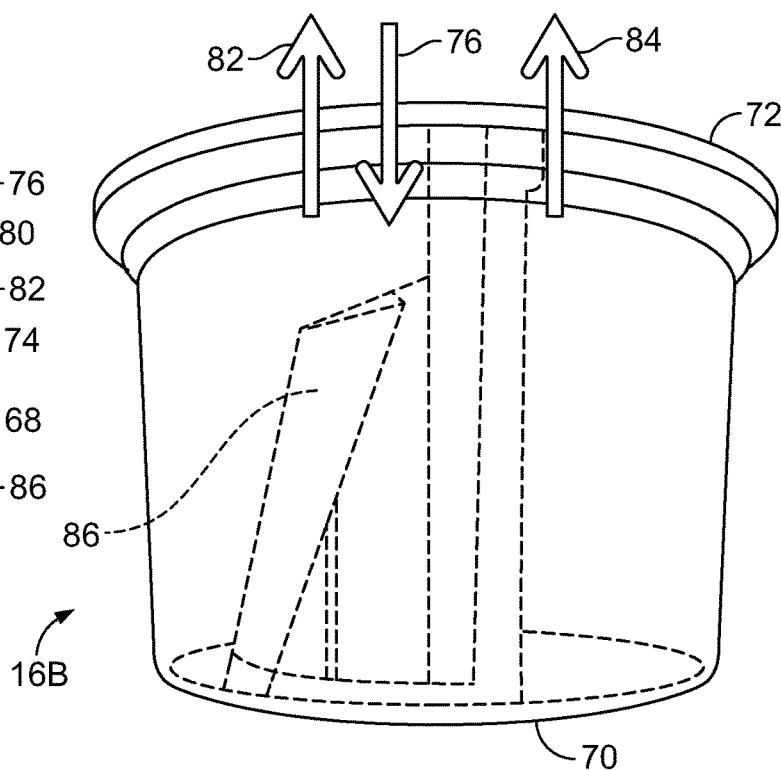
FIG. 8A is a front elevational view of the separation chamber of FIG. 8.
Figure 8B:
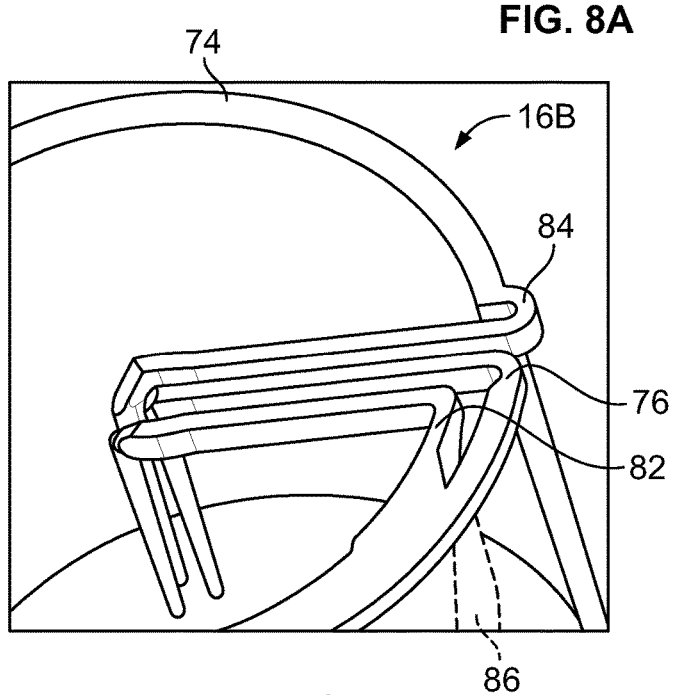
FIG. 8B is a top perspective view of the fluid flow path through the separation chamber of FIG. 8.

It should be understood that the separation chamber 16A illustrated in FIG. 7 is merely exemplary and that the separation chamber 16 may be differently configured without departing from the scope of the present disclosure. For example, FIGS. 8 and 8A show an alternative embodiment of a separation chamber 16B, while FIG. 8B illustrates the fluid flow path defined by the separation chamber 16B. The separation chamber 16B is similar to the separation chamber 16A except for the location at which the inlet 76 opens into the channel 74. In the separation chamber 16A of FIG. 7, the inlet 76 opens into the channel 74 adjacent to the first end wall portion 70 (while the outlets 82 and 84 open into the channel 74 adjacent to the second end wall portion 72), as best shown in FIGS. 7A and 7B. In contrast, the inlet 76 of the separation chamber 16B of FIG. 8 opens into the channel 74 adjacent to the second end wall portion 72 (along with the outlets 82 and 84), as best shown in FIGS. 8A and 8B.

Figure 9:
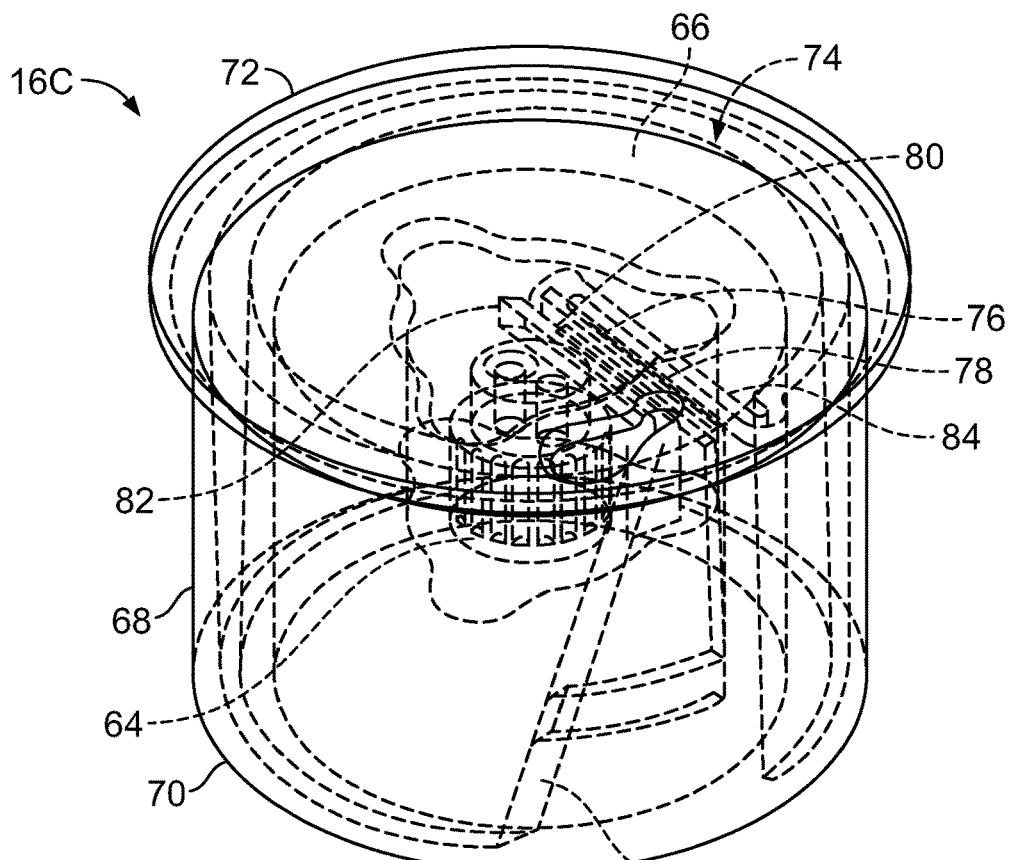
FIG. 9 is a perspective view of a third embodiment of an exemplary separation chamber of the fluid flow circuit of FIG. 5.
Figure 9A:
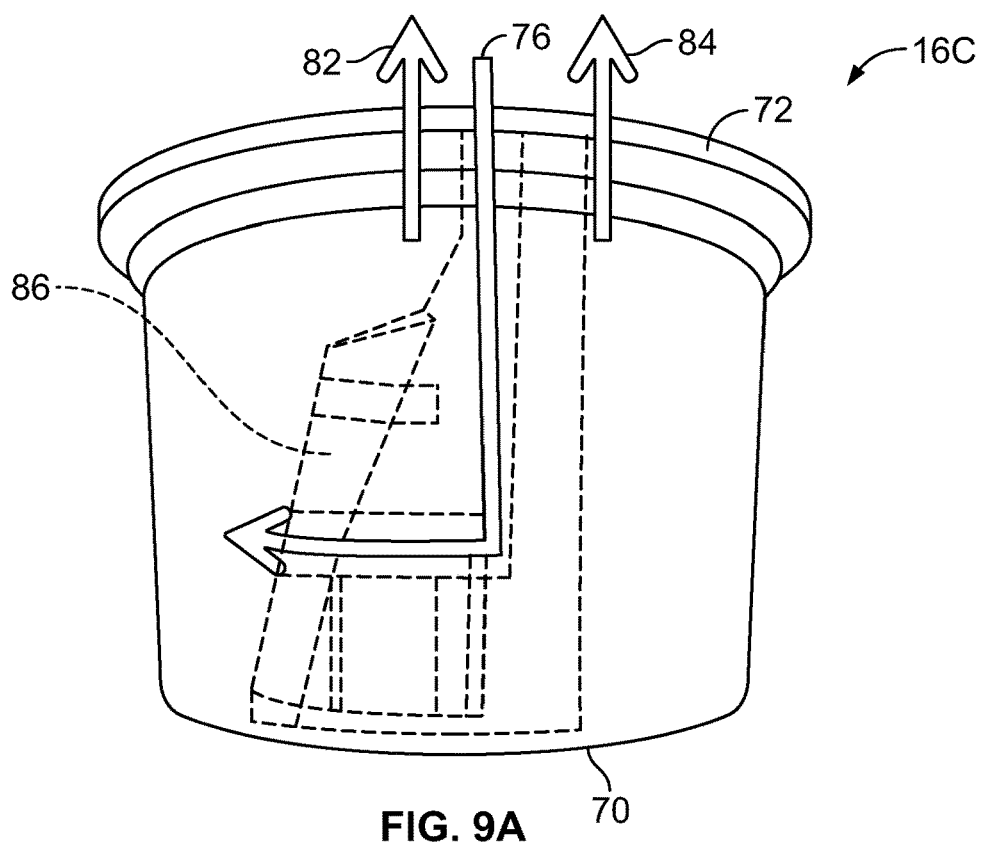
FIG. 9A is a front elevational view of the separation chamber of FIG. 9.

FIGS. 9 and 9A show a third exemplary embodiment of a separation chamber 16C suitable for incorporation into a fluid flow circuit 12. The separation chamber 16C is similar to the separation chambers 16A and 16B of FIGS. 7 and 8 except for the location at which the inlet 76 opens into the channel 74. In contrast to the inlets 76 of the separation chambers 16A and 16B of FIGS. 7 and 8, the inlet 76 of the separation chamber 16C of FIG. 9 opens into the channel 74 at an intermediate axial location that is spaced from the first and second end wall portion 70 and 72 (while the outlets 82 and 84 open into the channel 74 adjacent to the second end wall portion 72), as best shown in FIG. 9A. The inlet 76 may open into the channel 74 at a location that is closer to the first end wall portion 70 than to the second end wall portion 72, at a location that is closer to the second end wall portion 72 than to the first end wall portion 70, or at a location that is equally spaced between the first and second end wall portions 70 and 72.

Buffy coats flowed into the channel 74 separate into platelets and other cellular components as the separation chamber 16 is rotated about the rotational axis 22. The larger and/or heavier cellular components (i.e., red blood cells and white blood cells) move under the influence of centrifugal force toward the outer (high-g) wall portion 68, while the smaller and/or lighter components (i.e., plasma and platelets) remain closer to the inner (low-g) wall portion 66. In one embodiment, buffy coats introduced into the channel 74 via the inlet 76 will travel in a generally clockwise direction (in the orientation of FIG. 7) as the platelets separated from the other cellular components. The larger/heavier components continue moving in the clockwise direction as they travel the length of the channel 74 along the outer side wall portion 68, from the upstream end to the downstream end, where they exit the channel 74 via the second outlet 84. The platelets separated from the larger/heavier components reverse direction, moving counterclockwise along the inner side wall portion 66 to the first outlet 82, adjacent to the inlet 76.

As described above, the transition between the separated components may be referred to as the interface, and the location of the interface within the channel 74 of the separation chamber 16 can dynamically shift during fluid processing. If the location of the interface is too high (that is, if it is too close to the inner side wall portion 66 and the first outlet 82), red blood cells can flow into the first outlet 82, potentially adversely affecting the quality of the platelet product. On the other hand, if the location of the interface is too low (that is, if it resides too far away from the inner wall portion 66), the platelet collection efficiency of the centrifuge 14 may be impaired. The ideal or target interface location may be experimentally determined, which may vary depending on any of a number of factors (e.g., the configuration of the separation chamber 16, the rate at which the separation chamber 16 is rotated about the rotational axis 22, etc.).

As described above, the fluid separation device 10 may include an interface monitoring system and a controller with an interface control module to monitor and, as necessary, correct the position of the interface. In one embodiment, the separation chamber 16 is formed with a ramp 86 extending from the high-g wall portion 68 at an angle across a portion of the channel 74. Although it describes a flexible separation chamber, the general structure and function of the ramp 86 in monitoring the location of the interface may be better understood with reference to U.S. Pat. No. 5,632,893, which is incorporated herein by reference. In short, the location of the interface is visible on the angled ramp 86, which is transparent to light emitted by the light source 38 of the interface monitoring system. The amount of light transmitted through the platelets is greater than the amount of light transmitted through red blood cells, such that a sharp change in the amount of light received by the light detector 40 indicates the location of the interface. Accordingly, the amount of time that the light detector 40 receives a heightened amount of light as the ramp 86 rotates through the path of the light is indicative of the thickness of the platelet layer displayed on the ramp 86 and, hence, the position of the interface. If the interface is not properly positioned, then the controller of the fluid separation device 10 may take corrective action to move the interface to the proper location.

Figure 1:
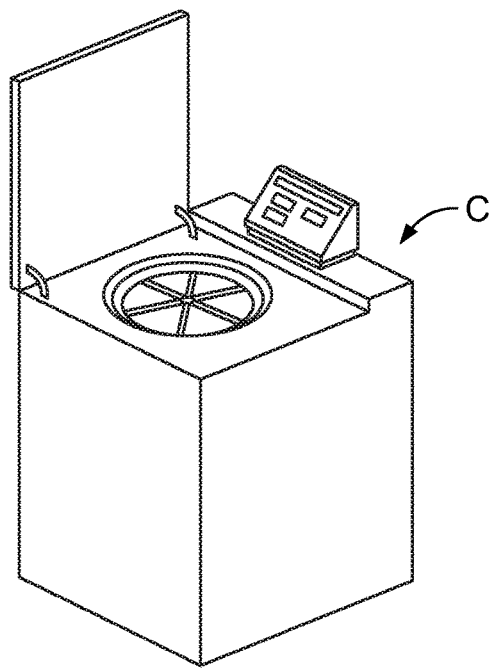
FIG. 1 is a perspective view of a floor centrifuge according to conventional design.
Figure 3:
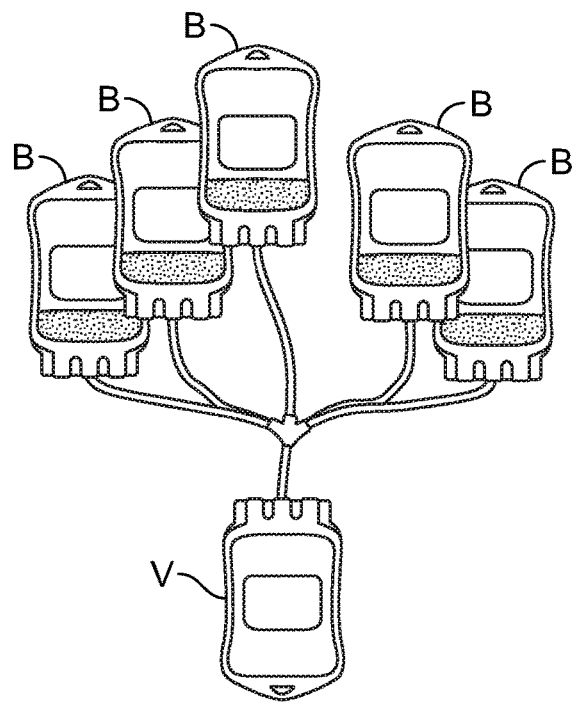
FIG. 3 is a front elevational view of an assembly for pooling five buffy coats into a single container according to conventional design.
Figure 2:
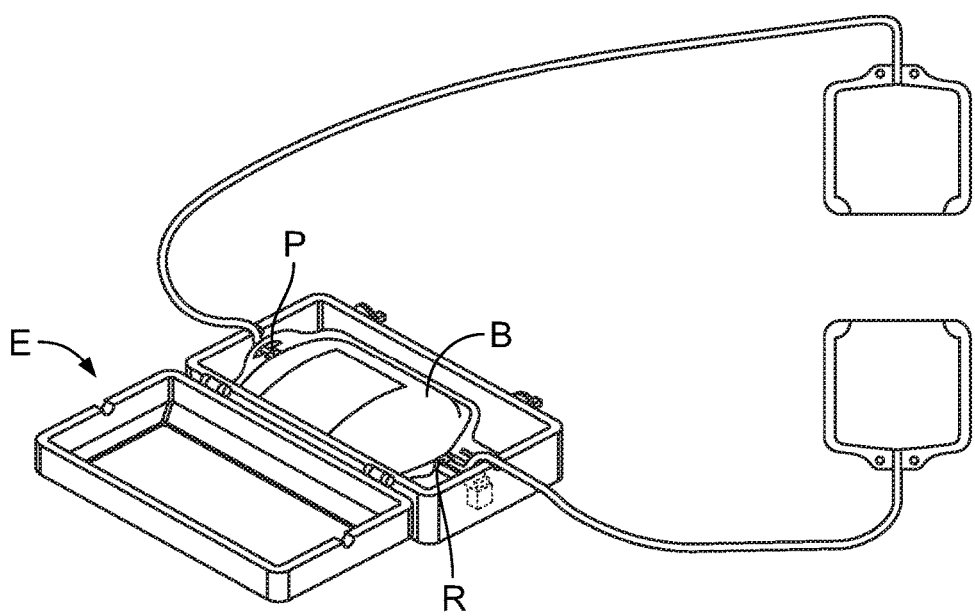
FIG. 2 is a perspective view of an expresser according to conventional design.

According to an exemplary method of using the fluid separation device 10 and fluid flow circuit 12, a supply of buffy coats may be generated according to any suitable approach, which may include (but is not limited to) the above-described conventional approach. A plurality of buffy coats may be pooled in a single fluid container, as in FIG. 3, with the fluid container 54 serving as a source container (FIG. 5). Plasma and/or a platelet additive solution may be added to the pooled buffy coats in the fluid container 54 prior to mounting the fluid flow circuit 12 to the fluid separation device 10. For example, in one embodiment, the pooled buffy coats may be mixed with an approximately equal volume of plasma and/or platelet additive solution to halve the hematocrit of the pooled buffy coats (from approximately 50% to approximately 25%), which may result in a platelet product having a desirable concentration of approximately $1300 \times 10^3$ platelets/A. In other embodiments, a different amount of plasma and/or platelet additive solution may be added to the buffy coats to reduce the hematocrit of the buffy coats to some other degree.

It is also within the scope of the present disclosure for the individual buffy coats to be diluted with plasma and/or platelet additive solution prior to being pooled together. If the individual buffy coats are mixed with plasma and/or platelet additive solution, then they may be directly connected to an inlet conduit 32 of the fluid flow circuit 12 (i.e., omitting the larger source container 54), such that the buffy coats are effectively pooled together as they flow through the inlet conduit 32. Alternatively, undiluted buffy coats (in separate containers) may be connected to the inlet conduit 32 and flowed into the separation chamber 16. An independent supply of plasma or platelet additive solution is conveyed into separation chamber 16 (e.g., using a separate pump, which is not illustrated), where it mixes with the buffy coats, thereby combining the dilution process with platelet harvesting.

In yet another embodiment, individual buffy coats may be sequentially flowed into and through the separation chamber 16, rather than ever being pooled. While the buffy coats are never pooled together, it will be appreciated that the resulting platelet product or products are the end result of an aggregation of a plurality of buffy coats.

As the buffy coats flow into and through the separation chamber 16 during a separation procedure, there is no specific limit to the volume of buffy coats that may be processed during a particular procedure. However, practical considerations may include the size of the fluid containers 54, 56, 58 required to accommodate the pooled buffy coats and/or the separated components and the amount of time available to carry out the procedure.

As the fluid separation device 10 may be used to carry out a variety of different separation procedures, an operator may be required to instruct the fluid separation device 10 to carry out a platelet product derivation or buffy coat separation procedure. In addition to selecting a particular protocol, the operator may also have the option of entering one or more parameters for the procedure, which informs the controller of the manner in which it is to control the other components of the fluid separation device 10 during the procedure. For example, it has been found that the flow rate of the buffy coats into the separation chamber 16 affects the separation efficiency of the centrifuge 14, so the operator may be prompted to input an inlet flow rate or a target separation efficiency.

Figure 10:
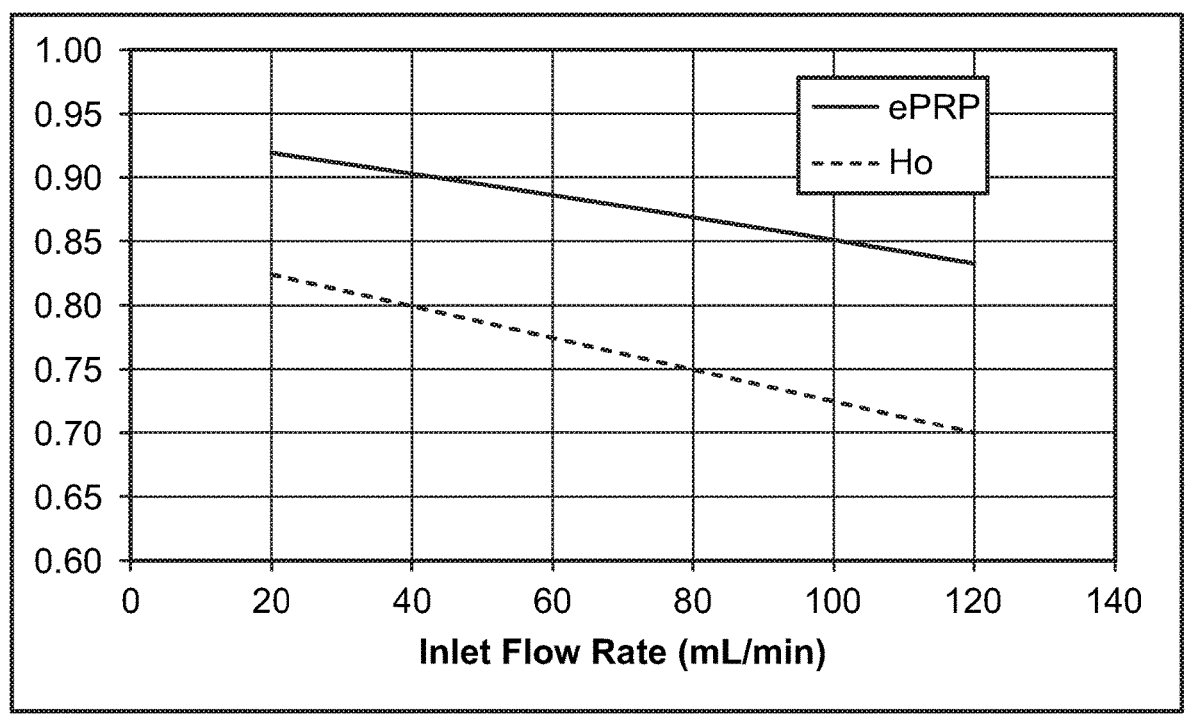
FIG. 10 is a chart showing the relationship between the rate at which buffy coat is conveyed into a separation chamber and platelet separation efficiency and the hematocrit of the components separated from the platelets.

FIG. 10 illustrates the calculated relationship between inlet flow rate and platelet separation efficiency (shown in a solid line) and the hematocrit of the fluid exiting the second outlet 84 of the separation chamber 16 (shown in broken lines). At a relatively low inlet flow rate (e.g., approximately 20 mL/min), the platelet separation efficiency may be greater than 90% during steady state separation, which does not account for platelet loss that may occur at the beginning and end of the procedure. In contrast, the platelet separation efficiency is between 80% and 85% during steady state operation for an inlet flow rate of approximately 120 mL/min. It is expected that the overall efficiency will be reduced by approximately 5% due to chamber residuals and filter losses. Thus, at a flow rate of 40 mL/min, an overall platelet separation efficiency may be treated as approximately 85% (which is calculated by reducing the 90% efficiency during steady state operation by a factor in view of platelet loss that may occur before and/or after steady state operation), in which case only 3.6 standard buffy coats (a total of approximately $3.6 \times 10^{11}$ platelets) may be required to produce a single-dose platelet product (containing approximately $3.0 \times 10^{11}$ platelets), compared to the conventional approach, which requires five buffy coats. Thus, when the procedure is carried out with an inlet flow rate of 40 mL/min, a supply of fifteen buffy coats may be provided to generate four single-dose platelet products. If it is acceptable for the procedure to be carried out with a lower inlet flow rate (which increases the time required to complete the procedure), then a ratio of as low as three buffy coats to one single-dose platelet product may be achieved. On the other hand, if it is preferred to increase the inlet flow rate (to decrease the time required to complete the procedure), then a ratio of buffy coats to single-dose platelet product of less than five (e.g., a 4:1 ratio) may still be achieved. Accordingly, the operator may be given the option to input the time required to complete the procedure, in which case the controller may calculate the expected platelet product yield and present the operator with the option to select a different completion time if the calculated platelet product yield is not acceptable.

When all of the required input has been entered and the fluid flow circuit 12 has been mounted to the fluid separation device 10, the controller may carry out an integrity check of the fluid flow circuit 12 to ensure the various components are properly connected and functioning. Following a successful integrity check, the fluid flow circuit 12 may be primed, such as pumping saline pumped from a saline bag (not illustrated) or by pumping an amount of the buffy coats through the separation chamber 16 in the centrifuge 14. In the illustrated embodiment, the conduits 34 and 36 connected to the outlets 82 and 84 of the separation chamber 16 are connected to each other by a conduit 88 associated with a valve or clamp 42 of the fluid separation device 10 (FIG. 5). Typically, the valve or clamp 42 is closed to prevent fluid communication between the two conduits 34 and 36 (thereby directing the separated platelets to the proper fluid container 56 and the other cellular components to the proper fluid container 58), but it may be advantageous to selectively allow fluid communication between the outlet conduits 34 and 36 during priming. For example, during priming of the fluid flow circuit 12, it may be advantageous to close a valve or clamp 44 associated with the conduit 34 and to open the valve or clamp 42 associated with the conduit 88. With the valves or clamps 42 and 44 so configured, any priming fluid exiting the separation chamber 16 via the conduit 34 is directed through the conduit 88 and the conduit 36 to the fluid container 58 (which may be referred to as a waste container), thereby preventing the priming fluid from entering the platelet collection container 56. It is also within the scope of the present disclosure for fluid flowing through the conduit 34 to be directed into the waste container 58 at any other time during a separation procedure.

In an alternative embodiment, the separation chamber 16 could be primed with the buffy coat solution, thus eliminating the need for a separate priming fluid and the need to direct priming fluid away from the platelet collection container 56.

When the fluid flow circuit 12 has been primed, fluid separation may begin. One of the pumps 48 operates to convey the buffy coats through an inlet conduit 32, where the buffy coats may pass through an air trap 60 and pressure sensor 46 associated with the inlet conduit 32. As described above, the buffy coats enter the channel 74 of the separation chamber 16 via the inlet 76, where the platelets are separated from the other cellular components by the centrifuge 14 rotating the separation chamber 16. The separated components continue flowing through the channel 74 of the separation chamber 16, with the platelets exiting the channel 74 via the first outlet 82 while the other cellular components exit the channel 74 via the second outlet 84. The conduit 34 of the fluid flow circuit 12 connected to the first outlet 82 may be associated with one of the pumps 50 of the fluid separation device 10, in which case the flow rate of separated platelets out of the channel 74 of the separation chamber 16 is controlled by the pump 50, while the flow rate of the other cellular components out of the second outlet 84 is equal to the difference between the inlet flow rate and the outlet flow rate of the separated platelets (by conservation of mass principles). In one embodiment, a majority of white blood cells may remain in the separation chamber 16 during the procedure, rather than exiting the channel 74.

The separated platelets flow through the conduit 34 to the collection container 56, optionally passing through a leukocyte removal filter 62 to decrease the amount of white blood cells in the resulting platelet product. While only a single collection container 56 is shown in FIG. 5, it is within the scope of the present disclosure for a plurality of fluid containers to be connected to the conduit 34, which may be advantageous if a large enough volume of buffy coats is being processed so as to generate multiple single-dose platelet products. Meanwhile, the cellular components separated from the platelets flow through the conduit 36 connected to the second outlet 84 of the separation chamber 16 into the waste container 58. These components may be collected for further processing (e.g., donation to a patient)

or may be discarded as a waste product. When all of the buffy coat has been processed, the collection container 56 may be sealed and separated from the remainder of the fluid flow circuit 12 for storage and/or further processing (e.g., donation to a patient), while the remainder of the fluid flow circuit 12 is removed from the fluid separation device 10 and discarded.

Figure 11:
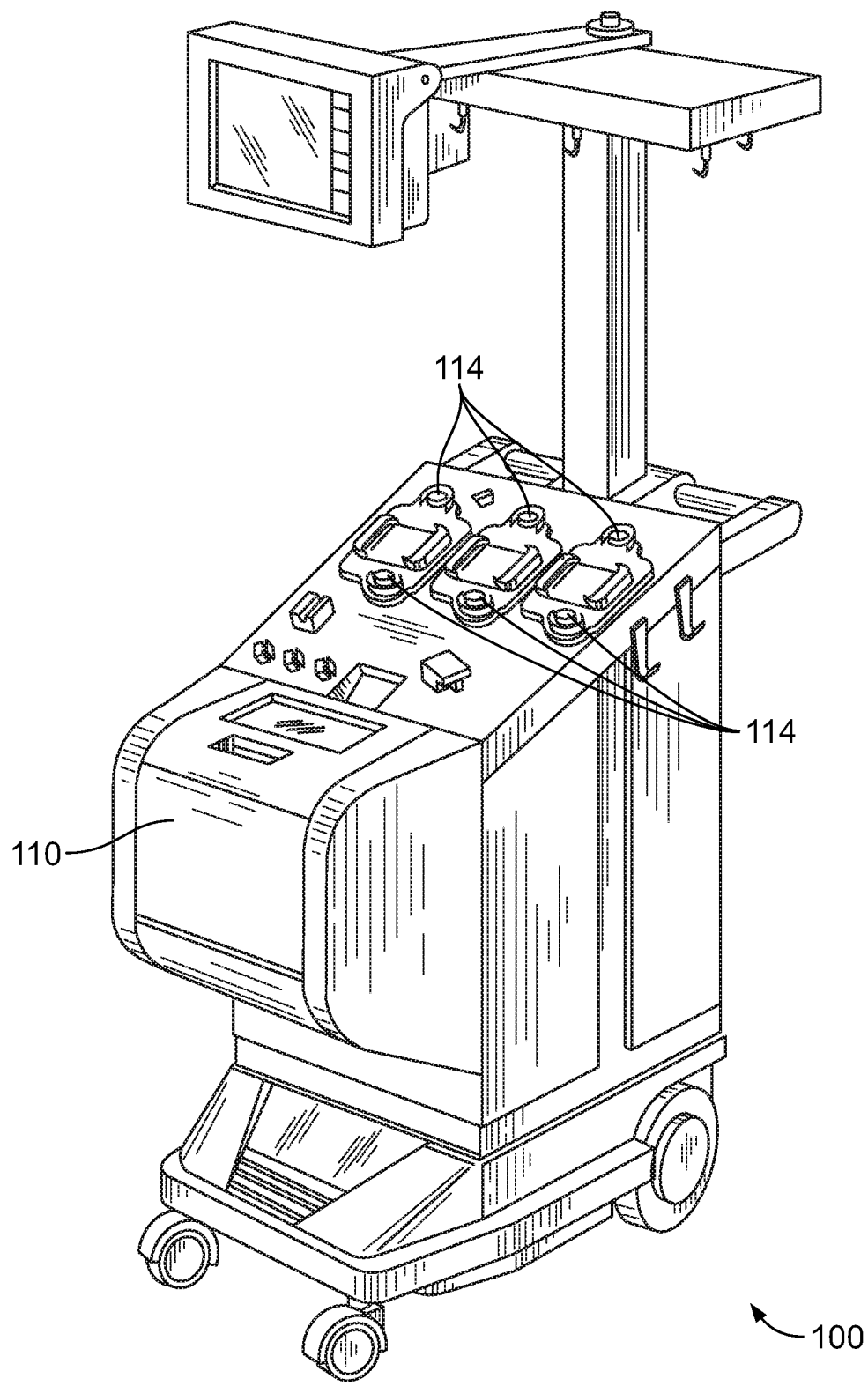
FIG. 11 is a perspective view of another embodiment of an exemplary fluid separation device that may be used in a buffy coat separation phase according to an aspect of the present disclosure.
Figure 12:
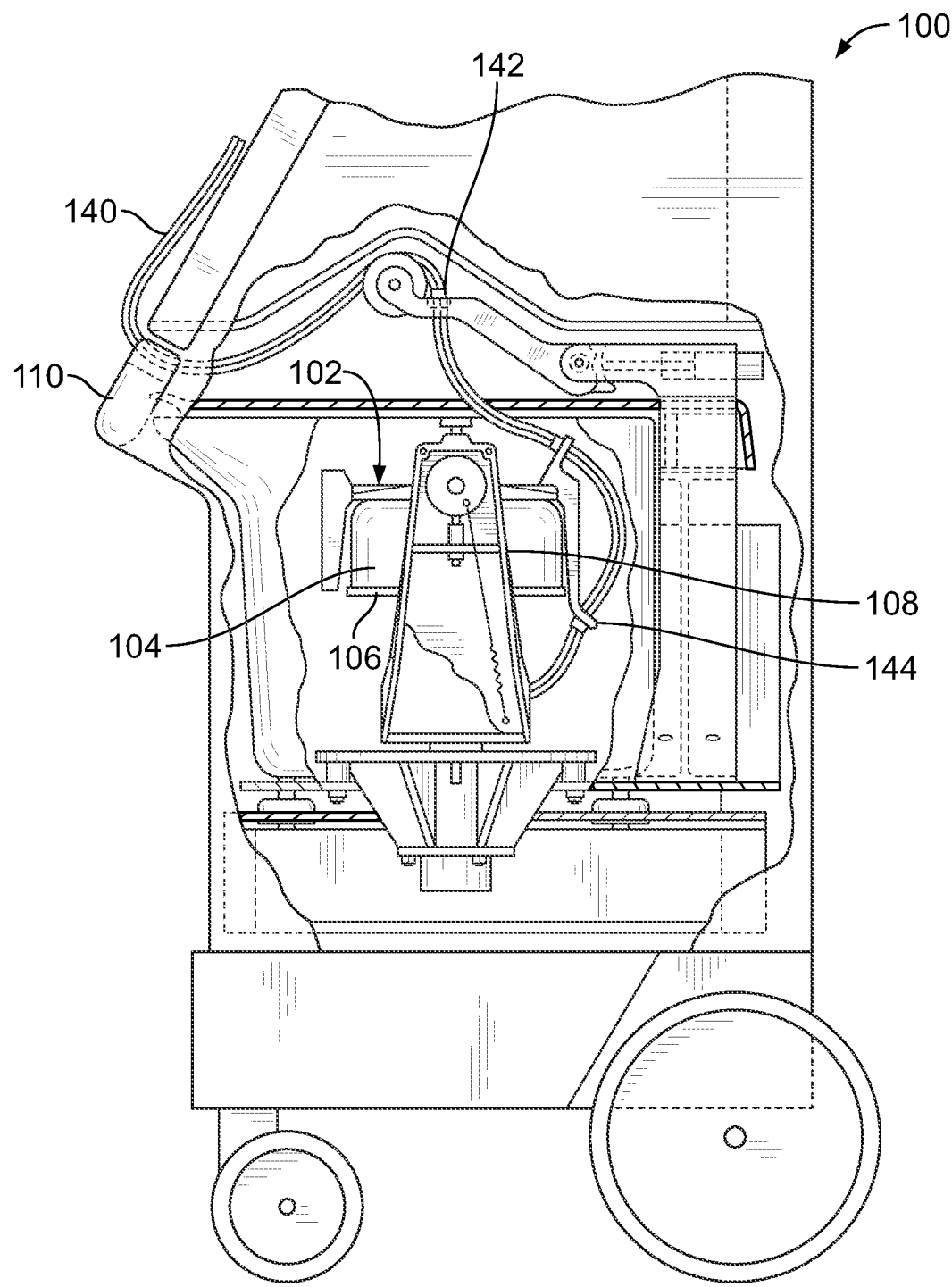
FIG. 12 is a side elevational view, with portions broken away and in section, of the fluid separation device of FIG. 11, with a centrifuge bowl and spool of the device being shown in their operating position.
Figure 13:
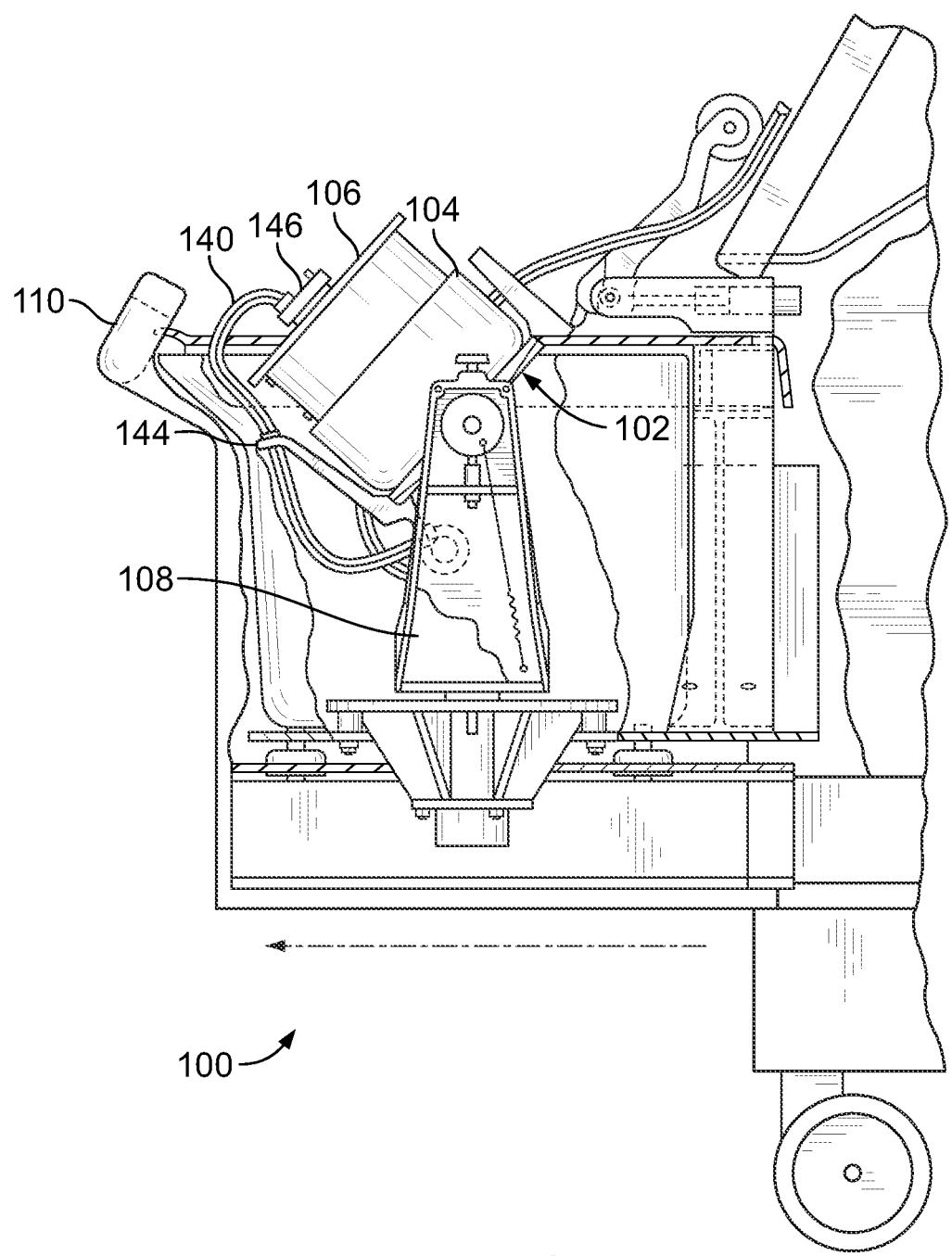
FIG. 13 is a side elevational view, with portions broken away and in section, of the fluid separation device of FIG. 11, with the centrifuge bowl and spool shown in an upright position for receiving a separation chamber.

FIGS. 11-13 show another embodiment of an exemplary fluid separation device 100 that may be used to carry out a platelet product derivation of buffy coat separation procedure according to the present disclosure. The fluid separation device 100 may be provided generally according to known design, such as the system currently marketed as the AMICUS® separator by Fenwal, Inc. of Lake Zurich, Ill., which is an affiliate of Fresenius Kabi AG of Bad Homburg, Germany, as described in greater detail in U.S. Pat. No. 5,868,696 or U.S. Patent Application Publication No. 2014/0045671, both of which are hereby incorporated herein by reference.

Figure 14:
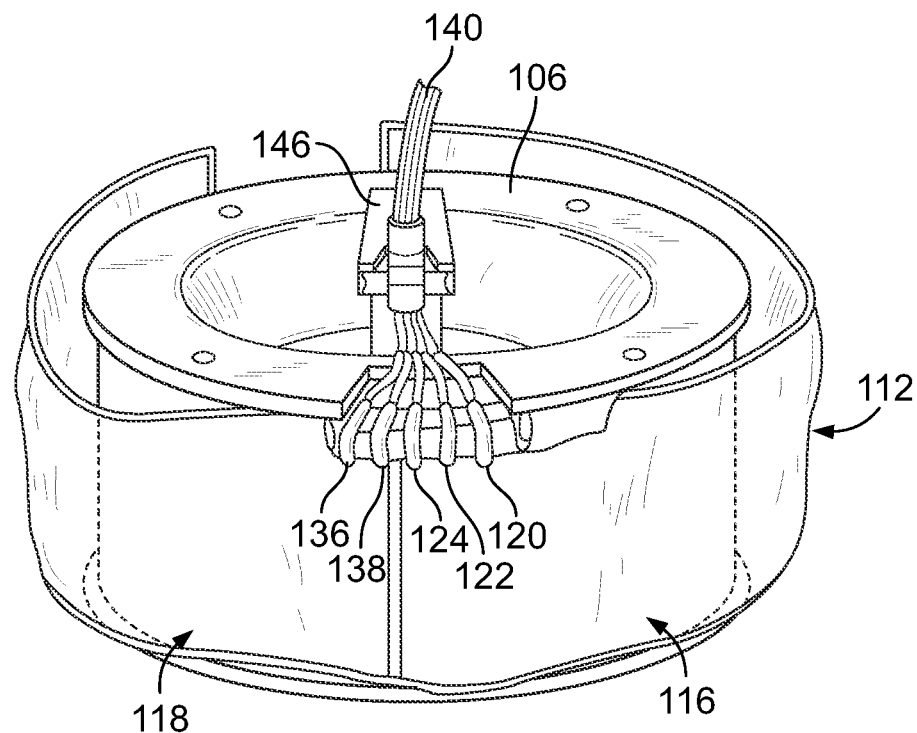
FIG. 14 is a top perspective view of the spool of the fluid separation device of FIG. 11 in its upright position and carrying a separation chamber of a fluid flow circuit.
Figure 15:
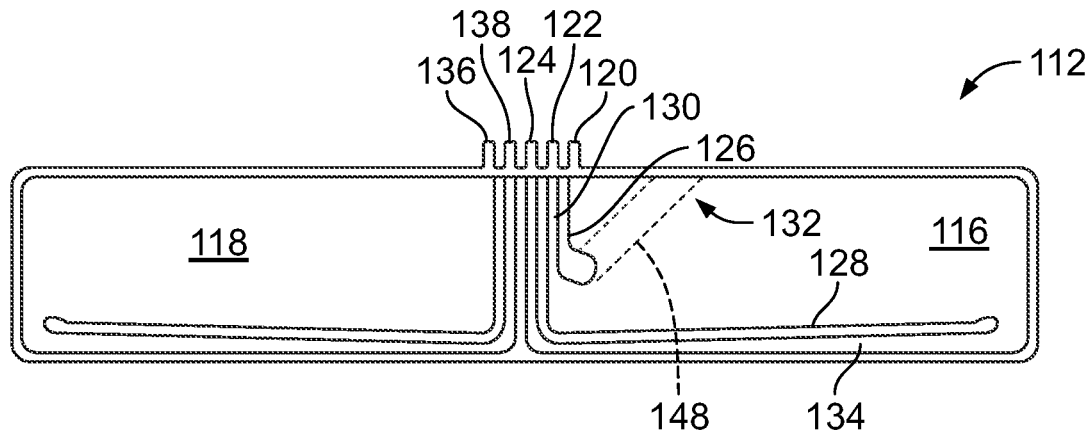
FIG. 15 is a schematic diagram of the separation chamber of FIG. 14.

The fluid separation device 100 includes a centrifuge 102 for centrifugally separating fluid components, and may be used to carry out a variety of different separation procedures in addition to being programmable to carry out a platelet product derivation or buffy coat separation protocol according to the present disclosure. The illustrated centrifuge 102 is of the type shown in U.S. Pat. No. 5,316,667, which is incorporated herein by reference. The centrifuge 102 comprises a generally annular bowl 104 and a generally cylindrical spool 106. The bowl 104 and spool 106 are pivoted on a yoke 108 between an operating position (FIG. 12) and a loading/unloading position (FIG. 13). The centrifuge 102 is illustrated as being housed within the interior of the fluid separation device 100, in which case a door 110 may be provided to allow access to the centrifuge 102 for loading and unloading a separation chamber 112 of a fluid flow circuit (FIGS. 14 and 15). The door 110 remains closed during operation to protect and enclose the centrifuge 102.

When in the loading/unloading position, the spool 106 can be accessed by movement at least partially out of the bowl 104, as FIG. 13 shows. In this position, the operator installs a separation chamber 112 (see FIG. 14) onto the spool 106. Closure of the spool 106 and bowl 104 encloses the separation chamber 112 for processing. When closed, the spool 106 and bowl 104 are pivoted into the operating position of FIG. 12 for rotation of the separation chamber 112 about an axis, as will be described in greater detail.

In contrast to the rigid separation chamber 16 of FIGS. 6-9A, the separation chamber 112 of FIGS. 14 and 15 is primarily flexible, such that its shape is defined by placing it in the annular gap between the spool 106 and bowl 104. In one embodiment, the fluid flow circuit and separation chamber 112 may be similar in form to the fluid flow circuit and separation chamber described in U.S. Patent Application Publication No. 2014/0045671, with a variety of components fluidly connected to the separation chamber 112 by flexible tubing conduits. As in the embodiment of FIG. 5, the fluid flow circuit may include a plurality of fluid containers fluidly connected to ports of the separation chamber 112, with at least one comprising a source container (for one or more buffy coats), another comprising a collection container (for receiving separated platelets), and another comprising a waste container (for receiving the cellular components separated from the platelets). The fluid flow circuit may also include a leukocyte removal filter and/or an air trap, as described above with respect to the fluid flow circuit 12 of FIG. 5. Selected portions of the fluid flow circuit may be configured to cooperate with pumps 114 of the fluid separation device 100 (e.g., tubing loops that are engaged by peristaltic pumps) to pump fluid through the fluid flow circuit.

FIG. 15 shows a representative embodiment of a multiple-stage separation chamber 112, which may be used in connection with the fluid separation device 100 of FIGS. 11-13. The separation chamber 112 shown in FIG. 15 is formed by a pair of flexible sheets joined at their perimeters to define first and second stages 116 and 118, allowing for either single- or multi-stage processing. However, only the first stage 116 is required for generating a platelet product according to one embodiment of the present disclosure, so it is within the scope of the present disclosure to provide a modified separation chamber including only a single stage.

As FIGS. 14 and 15 show, there are three ports 120, 122, and 124 extending through the sealed perimeter of the separation chamber 112 to allow fluid flow into and out of the first stage 116. Depending on the particular blood processing procedure, the ports may have different functionality but, in a platelet product derivation or buffy coat separation procedure according to the present disclosure, the port identified at 122 is used for conveying buffy coats into the first stage 116 (via a conduit connected to a source container of the fluid flow circuit). During such a platelet product derivation or buffy coat separation procedure, the other two ports 120 and 124 serve as outlet ports for passing separated fluid components from the first stage 116 to the fluid flow circuit (via separate conduits connected to the ports 120 and 124). More particularly, the first outlet port 120 conveys separated platelets from the first stage 116 to a collection container fluidly connected to the first outlet port 120, while the second outlet port 124 conveys the other cellular components from the first stage 116 to a waste container fluidly connected to the second outlet port 124.

As FIG. 15 shows, a first interior seal 126 is located between the inlet port 122 and the first outlet port 120, while a second interior seal 128 is located between the inlet port 122 and the second outlet port 124. The interior seals 126 and 128 form a fluid path or passage 130 (an inlet for buffy coats in an exemplary platelet product derivation or buffy coat separation procedure according to the present disclosure) and a low density collection path or region 132 in the first stage 116. The second seal 128 also forms a fluid passage 134, which serves as an outlet from the first stage 116 for the cellular components separated from platelets during an exemplary platelet product derivation or buffy coat separation procedure according to the present disclosure.

If multi-stage processing is required, one of the components will be transferred from the first stage 116 to the second stage 118 via a port 136 associated with the second stage 118. The component transferred to the second stage 118 is further fractionated into sub-components, with one of the sub-components being removed from the second stage 118 via an outlet port 138 and the other sub-component remaining in the second stage 118.

As shown in FIG. 14, the conduits connected to the ports 120, 122, 124, 136, and 138 are bundled together as a tubing umbilicus 140. The umbilicus 140 interconnects the first and second stages 116 and 118 with each other and with the components of the fluid flow circuit positioned outside of the centrifuge 102. As FIG. 12 shows, a non-rotating (zero omega) holder 142 holds the upper portion of the umbilicus 140 in a non-rotating position above the spool 106 and bowl 104. A holder 144 on the yoke 108 rotates the mid-portion of the umbilicus 140 at a first (one omega) speed about the suspended spool 106 and bowl 104. Another holder 146

(FIGS. 13 and 14) rotates the lower end of the umbilicus 140 at a second speed twice the one omega speed (the two omega speed), at which two omega speed the umbilicus 140 drives the rotation of the spool 106 and bowl 104. This known relative rotation of the umbilicus 140 keeps it untwisted, thus avoiding the need for rotating seals.

In the illustrated embodiment, a portion of the bowl 104 is light-transmissive and overlays a ramp 148 (FIG. 15) that extends radially inwardly at an angle toward the spool 106 to define a constricted passage. The ramp 148 discourages red blood cells from entering into the first outlet port 120 while displaying the relative positions of the separated components within the first stage 116 as the centrifuge 102 rotates the separation chamber 112 about a rotational axis. As described above with respect to the embodiment of FIGS. 1-9A, an interface monitoring system may direct light through the ramp, with the light being directed to a light detector that generates an output to a controller of the fluid separation device 100 that is indicative of the location of an interface between the separated components. If the controller determines that the interface is in the wrong location, then it can issue commands to the appropriate components of the fluid separation device 100 to modify their operation so as to move the interface to the proper location. The general structure and function of an exemplary ramp 148 and interface monitoring system are described in U.S. Pat. No. 5,632,893.

According to an exemplary method of using the fluid separation device 100, a supply of buffy coats may be generated according to any suitable approach, which may include (but is not limited to) the previously described conventional approach. A plurality of buffy coats may be pooled in a single fluid container, as in FIG. 3, with the fluid container serving as a source container. Plasma and/or a platelet additive solution may be added to the pooled buffy coats in the source container prior to mounting the fluid flow circuit to the fluid separation device 100. For example, in one embodiment, the pooled buffy coats may be mixed with an approximately equal volume of plasma and/or platelet additive solution to halve the hematocrit of the pooled buffy coats (from approximately 50% to approximately 25%), which may result in a platelet product having a desirable concentration of approximately $1300 \times 10^3$ platelets/A. In other embodiments, a different amount of plasma and/or platelet additive solution may be added to the buffy coats to reduce the hematocrit of the buffy coats to some other degree. It is also within the scope of the present disclosure for the individual buffy coats to be diluted with plasma and/or platelet additive solution prior to being pooled together. If the individual buffy coats are mixed with plasma and/or platelet additive solution, then they may be directly connected to an inlet conduit of the fluid flow circuit (i.e., omitting the larger source container), such that the buffy coats are effectively pooled together as they flow through the inlet conduit. Alternatively, individual buffy coats may be sequentially flowed into and through the separation chamber 112 without being pooled.

As the buffy coats flow into and through the separation chamber 112 during a separation procedure, there is no specific limit to the volume of buffy coats that may be processed during a particular procedure. However, practical considerations may include the size of the fluid containers required to accommodate the pooled buffy coats and/or the separated components and the amount of time available to carry out the procedure.

As the fluid separation device 100 may be used to carry out a variety of different separation procedures, an operator may be required to instruct the fluid separation device 100 to carry out a platelet product derivation or buffy coat separation procedure. In addition to selecting a particular protocol, the operator may also have the option of entering one or more parameters for the procedure, which informs the controller of the manner in which it is to control the other components of the fluid separation device 100 during the procedure. For example, as described above with respect to the embodiment of FIGS. 1-9A, it has been found that the flow rate of the buffy coats into the separation chamber 112 affects the separation efficiency of the centrifuge 102, so the operator may be prompted to input an inlet flow rate or a target separation efficiency or the time allowed for the fluid separation device 100 to complete the procedure.

When all of the required input has been entered and the fluid flow circuit has been mounted to the fluid separation device 100 with the separation chamber 112 in the centrifuge 102, the controller may carry out an integrity check of the fluid flow circuit to ensure the various components are properly connected and functioning. Following a successful integrity check, the fluid flow circuit may be primed, such as pumping saline pumped from a saline bag or by pumping an amount of the buffy coats through the separation chamber 112 in the centrifuge 102. Any priming fluid may be directed away from the platelet collection container (e.g., into the waste container) to avoid compromising the quality of the platelet product. Alternatively, the separation chamber 112 could be primed with the buffy coat solution, thus eliminating the need for a separate priming fluid.

When the fluid flow circuit has been primed, fluid separation may begin. One or more of the pumps 114 of the fluid separation device 100 operates to convey the buffy coats through an inlet conduit connected to the inlet port 122. As described above, the buffy coats enter the first stage 116 of the separation chamber 112 via the inlet port 122, where the platelets are separated from the other cellular components by the centrifuge 102 rotating the separation chamber 112. The separated components continue flowing through the first stage 116 of the separation chamber 112, with the platelets exiting the first stage 116 via the first outlet port 120 while the other blood components exit the first stage 116 via the second outlet port 124.

The separated platelets flow through the conduit connected to the first outlet port 120 to one or more collection containers, optionally passing through a leukocyte removal filter to decrease the amount of white blood cells in the resulting platelet product. Meanwhile, the cellular components separated from the platelets flow through the conduit connected to the second outlet port 124 into a waste container or containers. While this fluid container is referred to as a waste container, it should be understood that the components flowed into the container may be treated as a waste product or retained for further processing (e.g., donation to a patient). When all of the buffy coat has been processed, the collection container may be sealed and separated from the remainder of the fluid flow circuit for storage and/or further processing (e.g., donation to a patient), while the remainder of the fluid flow circuit is removed from the fluid separation device 100 and discarded.

Aspects of the present subject matter described above may be beneficial alone or in combination with one or more other aspects. Without limiting the foregoing description, in accordance with one aspect of the subject matter herein, there is provided a method of deriving a platelet product from a plurality of buffy coats. The method includes conveying a plurality of buffy coats into a centrifuge, where platelets are continuously separated from the other cellular blood components of the plurality of buffy coats. The separated platelets are collected as a platelet product.

In accordance with another aspect which may be used or combined with the immediately preceding aspect, plasma or platelet additive solution is added to the plurality of buffy coats before conveying them into the centrifuge.

In accordance with another aspect which may be used or combined with any of the preceding aspects, the separated platelets are conveyed through a leukocyte removal filter before collecting them as a platelet product.

In accordance with another aspect which may be used or combined with any of the preceding aspects, the plurality of buffy coats is conveyed into a rigid separation chamber in the centrifuge.

In accordance with another aspect which may be used or combined with any of the first through third aspects, the plurality of buffy coats is conveyed into a flexible separation chamber in the centrifuge.

In accordance with another aspect which may be used or combined with any of the preceding aspects, the plurality of buffy coat is separated from other blood components by centrifugal separation, with the blood and the plurality of buffy coats being processed in different centrifuges.

In accordance with another aspect which may be used or combined with the immediately preceding aspect, the blood and plurality of buffy coats are processed in differently configured centrifuges.

In accordance with another aspect which may be used or combined with any of the preceding aspects, blood is processed to separate buffy coat from other blood components, with the processing of blood to separate buffy coat from other blood components being repeated fewer than four times to generate the plurality of buffy coats.

In accordance with another aspect which may be used or combined with the immediately preceding aspect, the processing of blood to separate buffy coat from other blood components is repeated three times.

In accordance with another aspect which may be used or combined with the eighth aspect, the processing of blood to separate buffy coat from other blood components is repeated two times.

In accordance with another aspect which may be used or combined with any of the first through seventh aspects, the plurality of buffy coats is generated by processing blood to separate buffy coat from other blood components, which processing of the blood is repeated at least four times to generate additional buffy coats. Generating such an amount of buffy coats allows for the collection of a plurality of single-dose platelet products.

In accordance with another aspect which may be used or combined with any of the preceding aspects, the plurality of buffy coats is pooled prior to conveying them into the centrifuge.

In accordance with another aspect which may be used or combined with any of the first through eleventh aspects, the plurality of buffy coats is sequentially conveyed into the centrifuge.

In accordance with another aspect, there is provided a method of deriving a platelet product from a plurality of buffy coats. The method includes processing blood in a first centrifuge to separate buffy coat from other blood components. The process of separating buffy coat from other blood components is repeated multiple times to generate additional buffy coats. The buffy coats are conveyed into a second centrifuge that is differently configured from the first centrifuge, where platelets are separated from the other cellular blood components of the buffy coats. The separated platelets are collected as a platelet product.

In accordance with another aspect which may be used or combined with the immediately preceding aspect, plasma or platelet additive solution is added to the buffy coats before conveying them into the second centrifuge.

In accordance with another aspect which may be used or combined with any of the preceding two aspects, the separated platelets are conveyed through a leukocyte removal filter before collecting them as a platelet product.

In accordance with another aspect which may be used or combined with any of the preceding three aspects, the buffy coats are conveyed into a rigid separation chamber in the second centrifuge.

In accordance with another aspect which may be used or combined with any of the fourteenth through sixteenth aspects, the buffy coats are conveyed into a flexible separation chamber in the second centrifuge.

In accordance with another aspect which may be used or combined with any of the preceding five aspects, the processing of blood to separate buffy coat from other blood components is repeated fewer than four times.

In accordance with another aspect which may be used or combined with the immediately preceding aspect, the processing of blood to separate buffy coat from other blood components is repeated three times.

In accordance with another aspect which may be used or combined with the nineteenth aspect, the processing of blood to separate buffy coat from other blood components is repeated two times.

In accordance with another aspect which may be used or combined with any of the preceding eight aspects, platelets are continuously separated from other cellular blood components of the pooled buffy coats in the second centrifuge.

In accordance with another aspect which may be used or combined with any of the fourteenth through eighteenth aspects, the processing of blood to separate buffy coat from other blood components is repeated at least four times, with a plurality of single-dose platelet products being collected.

In accordance with another aspect which may be used or combined with any of the fourteenth through twenty-third aspects, the buffy coats are pooled prior to conveying them into the second centrifuge.

In accordance with another aspect which may be used or combined with any of the fourteenth through twenty-third aspects, the buffy coats are sequentially conveyed into the second centrifuge.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A method of deriving a platelet product from a plurality of buffy coats comprising:
conveying a plurality of buffy coats into a centrifuge;
continuously separating platelets from other cellular blood components of the plurality of buffy coats in the centrifuge; and collecting the separated platelets as a platelet product, wherein
the platelets are separated from the other cellular blood components of the plurality of buffy coats in the centrifuge at a rate at which a single-dose platelet product is produced from at least three buffy coats and fewer than five buffy coats, and
the centrifuge is continuously operated to produce at least three single-dose platelet products.

2. The method of claim 1, further comprising adding plasma or platelet additive solution to said plurality of buffy coats before conveying said plurality of buffy coats into the centrifuge.

3. The method of claim 1, further comprising conveying said separated platelets through a leukocyte removal filter before collecting the separated platelets as a platelet product.

4. The method of claim 1, wherein said conveying said plurality of buffy coats into the centrifuge includes conveying said plurality of buffy coats into a rigid separation chamber.

5. The method of claim 1, wherein said conveying said plurality of buffy coats into the centrifuge includes conveying said plurality buffy coats into a flexible separation chamber.

6. The method of claim 1, further comprising centrifuging blood to separate buffy coat from other blood components before conveying said plurality of buffy coats into the centrifuge, wherein the blood and the plurality of buffy coats are processed in different centrifuges.

7. The method of claim 6, wherein the blood and the plurality of buffy coats are processed in differently configured centrifuges.

8. The method of claim 6, wherein
the blood is processed in a floor centrifuge, and
the plurality of buffy coats are processed in a continuous-separation centrifuge.

9. The method of claim 1, further comprising pooling said plurality of buffy coats prior to conveying said plurality of buffy coats into the centrifuge.

10. The method of claim 1, wherein said conveying said plurality of buffy coats into the centrifuge includes sequentially conveying said plurality of buffy coats into the centrifuge.

11. The method of claim 1, wherein the plurality of buffy coats are conveyed into the centrifuge at an inlet flow rate of no more than 120 mL/min.

12. A method of deriving a platelet product from a plurality of buffy coats comprising:
conveying a plurality of buffy coats into a centrifuge;
continuously separating platelets from other cellular blood components of the plurality of buffy coats in the centrifuge; and
collecting the separated platelets as a platelet product, wherein the plurality of buffy coats are conveyed into the centrifuge at an inlet flow rate of no more than 120 mL/min such that the platelets are separated from the other cellular blood components of the plurality of buffy coats in the centrifuge at a rate at which a single-dose platelet product is produced from at least three buffy coats and fewer than five buffy coats.

13. The method of claim 12, further comprising adding plasma or platelet additive solution to said plurality of buffy coats before conveying said plurality of buffy coats into the centrifuge.

14. The method of claim 12, further comprising conveying said separated platelets through a leukocyte removal filter before collecting the separated platelets as a platelet product.

15. The method of claim 12, wherein said conveying said plurality of buffy coats into the centrifuge includes conveying said plurality of buffy coats into a rigid separation chamber.

16. The method of claim 12, wherein said conveying said plurality of buffy coats into the centrifuge includes conveying said plurality buffy coats into a flexible separation chamber.

17. The method of claim 12, further comprising centrifuging blood to separate buffy coat from other blood components before conveying said plurality of buffy coats into the centrifuge, wherein the blood and the plurality of buffy coats are processed in different centrifuges.

18. The method of claim 17, wherein
the blood is processed in a floor centrifuge, and
the plurality of buffy coats are processed in a continuous-separation centrifuge.

* * * * *